United States Patent
Duffer et al.

(10) Patent No.: US 6,669,933 B2
(45) Date of Patent: Dec. 30, 2003

(54) METHOD AND COMPOSITIONS FOR COLORING HAIR

(75) Inventors: Dalal Ibrahim Esber Duffer, North Brunswick, NJ (US); Louann Christine Vena, Scotch Plains, NJ (US); Minmin Tian, North Brunswick, NJ (US); Shailendra Kumar Singh, Edison, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 36 days.

(21) Appl. No.: 09/852,982

(22) Filed: May 10, 2001

(65) Prior Publication Data

US 2003/0028979 A1 Feb. 13, 2003

(51) Int. Cl.[7] .............................. A61K 7/06; A61K 7/135
(52) U.S. Cl. ........................ 424/70.1; 424/401; 424/64; 8/406; 8/408
(58) Field of Search ............................... 424/70.1, 401, 424/62; 8/406, 408

(56) References Cited

U.S. PATENT DOCUMENTS

| | | | |
|---|---|---|---|
| 3,415,608 A | 12/1968 | Tucker | 8/10.2 |
| 3,931,912 A | 1/1976 | Hsiung | |
| 3,957,424 A | 5/1976 | Zeffren | 8/10.2 |
| 4,168,952 A | 9/1979 | Buhler | 8/10.1 |
| 4,337,061 A | 6/1982 | Buguat | 8/405 |
| 4,775,527 A | 10/1988 | Bires | 424/62 |
| 4,832,767 A | 5/1989 | Eller | 8/416 |
| 4,857,071 A | 8/1989 | Anderson | 8/414 |
| 4,927,627 A | 5/1990 | Schrader | 424/62 |
| 4,935,032 A | 6/1990 | Grollier | 8/414 |
| RE33,786 E | 1/1992 | Pohl | 8/406 |
| 5,104,413 A | 4/1992 | Ikeda | 8/405 |
| 5,340,367 A | 8/1994 | Schultz | 8/432 |
| 5,393,305 A | 2/1995 | Cohen | 8/406 |
| 5,718,731 A | 2/1998 | Loewe | 8/409 |
| 5,843,193 A | 12/1998 | Hawkins | 8/408 |
| 6,022,381 A | 2/2000 | Dias | 8/406 |
| 6,102,974 A | 8/2000 | Braun | 8/411 |
| 6,106,578 A | 8/2000 | Jones | 8/406 |
| 6,110,474 A | 8/2000 | Roman | 424/401 |
| 6,146,429 A | 11/2000 | Gast | 8/408 |

Primary Examiner—Thurman K. Page
Assistant Examiner—Lakshmi Channavajjala
(74) Attorney, Agent, or Firm—Julie Blackburn

(57) ABSTRACT

An aqueous hair color composition for oxidatively coloring hair in twelve minutes or less, wherein said composition is prepared by combining a dye mixture and a developer mixture, said aqueous hair color composition comprising 0.01–2.0% (combined weight) of the total composition of primary intermediates and couplers, a free alkalinity concentration of 0.20–0.75 meq/gram, and a hydrogen peroxide concentration of 4–6% by weight of the total composition; and a hair coloring kit containing separate containers of an aqueous dye mixture and an aqueous developing mixture for use with said dye mixture.

34 Claims, No Drawings

METHOD AND COMPOSITIONS FOR COLORING HAIR

TECHNICAL FIELD

The invention is in the field of compositions and methods for oxidative dyeing of hair.

BACKGROUND OF THE INVENTION

Commercially available hair color generally falls into one of three categories: permanent, semi-permanent, or temporary. The term "permanent" generally refers to oxidative hair color, which provides hair color that lasts about four to six weeks. Oxidative hair color is usually sold in the form of a two component kit. The preferred kits have one container filled with an aqueous alkaline composition in the liquid, gel, or creme form that contains oxidative dyes, an alkalizing agent which is most often ammonium hydroxide, optionally one or more fatty acids. In the other container is a developer composition that contains an oxidizing agent, usually hydrogen peroxide. The two components are mixed immediately prior to use and applied to hair. This mixture is left on the hair for an appropriate period of time, generally 20 to 60 minutes, then rinsed off with water.

While permanent hair color provides the longest lasting results, many consumers feel that waiting 20 to 60 minutes for hair to color is simply too long. Accordingly, the time commitment deters many potential consumers from coloring their hair. Obviously if the time period required for oxidatively coloring hair could be reduced significantly, this would make coloring the hair much more attractive to consumers.

Efforts to reduce the time to permanently color hair have met with limited success. Some attempts have involved increasing the dye concentration in the hair color mixture to achieve greater color deposit in a shorter period of time. One example of this type of dye is a Clairol product, For Men Only, which is a shampoo in hair color targeted to gray haired men who desire to blend away their gray hair in a five minute process. While the Clairol product will deposit color in five minutes and blend away gray, its biggest drawback is that it is strictly a tone-on-tone color. That means that no lifting of the hair occurs, and at most the hair can only be colored the same color or a darker color than the original color. Revlon also sells a commercial product hair color product for men that colors hair in five minutes. While this product provides permanent color to hair it does not provide any "lift". Thus, the haircolor will only color the hair the same shade or a darker shade.

A Japanese product called Lavenus advertises 10 minute color. However this product provides lift or bleaching only, and is only capable of lightening the hair by bleaching the melanin out of the hair fibers.

In order to permanently color hair in shorter periods of time, say less than 10 or 12 minutes, without restriction as to shade, it is necessary to both bleach the melanin out of the hair fibers and color the hair in the desired color in the given time frame.

It has been discovered that time required to achieve lift and color the hair can be significantly reduced if the composition ultimately applied to the hair has three very specific parameters, namely the composition as applied to the hair must have a total concentration of hair dyes (primary intermediates and couplers) ranging from about 0.01–2.0% by weight of the total composition, a free alkalinity concentration of 0.20–0.75 meq/gram, and a hydrogen peroxide concentration of 4.0 to 6.0% by weight of the total composition.

It is an object of the invention to provide a method and compositions for oxidatively coloring hair in twelve, preferably ten, minutes or less.

It is further object of the invention to provide a method and compositions for permanently coloring hair in ten minutes or less without damaging or drying hair.

It is a further object of the invention to provide a hair dye composition wherein the mixture as applied to hair contains very specific ranges of alkalizing agent, dye, and hydrogen peroxide, in order to achieve permanent hair color in twelve, preferably ten, minutes or less.

SUMMARY OF THE INVENTION

The invention is directed to a aqueous hair color composition for oxidatively coloring hair in ten to twelve minutes or less, wherein said composition is prepared by combining a dye mixture and a developer mixture, said aqueous hair color composition comprising:
 a) 0.01–2.0% (combined weight) of the total composition of primary intermediates and couplers,
 b) a free alkalinity concentration of 0.20 to 0.75 meq/gram, and
 c) a hydrogen peroxide concentration of 4.0 to 6.0% by weight of the total composition.

The invention is also directed to a hair coloring kit containing separate containers of:
I. an aqueous dye mixture comprising:
 a) primary intermediates and color couplers, and
 b) an alkalizing agent; and
II. an aqueous hydrogen peroxide containing developing mixture for use with said dye mixture;
wherein when the aqueous hair dye mixture is combined with the aqueous developing mixture, the resulting aqueous hair color composition comprises:
 a) 0.01–2.0% (combined weight) of the total composition of primary intermediates and couplers,
 b) a free alkalinity concentration of 0.20–0.75 meq/gram, and
 c) a hydrogen peroxide concentration of 4.0 to 6.0% by weight of the total composition.

DETAILED DESCRIPTION

I. The Aqueous Haircolor Composition

The aqueous hair color composition of the invention is formed by combining a hair dye mixture and a developer mixture. The hair dye mixture and the developer mixture will be described separately as to their constitutents, followed by a description of the aqueous hair color composition that is obtained when the hair dye mixture and developer mixture are combined in order to achieve the objectives of the invention.

A. The Hair Dye Mixture

The hair dye mixture may be in the form of a liquid or creme. The term "crème" means a viscous liquid or semi-solid that does not readily drip when applied to the hair. It may be in the solution or emulsion form. Preferably, the hair dye mixture is in the form of an emulsion, more preferably a water-in-oil or oil-in-water emulsion. Most preferred is where the mixture is in the form of an oil-in-water emulsion. Such types of emulsion may contain from about 35–98% water and 2–65% oil, all percentages by weight of the total composition. The hair dye mixture may also contain other ingredients, as set forth herein.

1. Primary Intermediates.

The claimed composition comprises one or more primary intermediates. Suggested ranges of primary intermediates are 0.0001–6%, preferably 0.0005–5.5%, more preferably 0.001–5% by weight of the total composition. Such primary intermediates are well known for use in hair color, and include ortho or para substituted aminophenols or phenylenediamines, such as para-phenylenediamines of the formula:

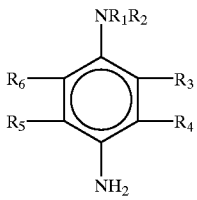

wherein $R^1$ and $R_2$ are each independently hydrogen, $C_{1-6}$ alkyl, or $C_{1-6}$ alkyl substituted with one or more hydroxy, methoxy, methylsulphonylamino, aminocarbonyl, furfuryl, unsubstituted phenyl, or amino substituted phenyl groups; $R_3$, $R_4$, $R_5$, and $R_6$ are each independently hydrogen, $C_{1-6}$ alkyl, $C_{1-6}$ alkoxy, halogen, or $C_{1-6}$ alkyl substituted with one or more hydroxy or amino groups.

Specific examples of suitable primary intermediates include para-phenylenediamine, 2-methyl-1,4-diaminobenzene, 2,6-dimethyl-1,4-diaminobenzene, 2,5-dimethyl-1,4-diaminobenzene, 2,3-dimethyl-1,4-diaminobenzene, 2-chloro-1,4-diaminobenzene, 2-methoxy-1,4-diaminobenzene, 1-phenylamino-4-aminobenzene, 1-dimethylamino-4-aminobenzene, 1-diethylamino-4-aminobenzene, 1-bis(beta-hydroxyethyl)amino-4-aminobenzene, 1-methoxyethylamino-4-aminobenzene, 2-hydroxymethyl-1,4-diaminobenzene, 2-hydroxyethyl-1,4-diaminobenzene, 2-isopropyl-1,4-diaminobenzene, 1-hydroxypropylamino-4-aminobenzene, 2,6-dimethyl-3-methoxy-1,4-diaminobenzene, 1-amino-4-hydroxybenzene, and derivatives thereof, and acid or basic salts thereof Preferred primary intermediates are p-phenylenediamine, p-aminophenol, o-aminophenol, N,N-bis(2-hydroxyethyl)-p-phenylenediamine, 2,5-diaminotoluene, their salts and mixtures thereof.

2. Color Coupler

The dye mixture preferably comprises from about 0.0001–10%, more preferably 0.0005–8%, most preferably 0.001–7% by weight of the total composition of one or more color couplers which are dyestuff components. Suitable color couplers include, for example, those having the general formula:

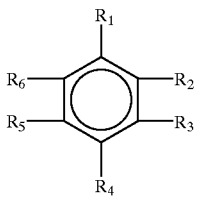

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, catechol, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methyl pyrazolone, 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3[(beta-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino) benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamionphenoxyethanol, and mixtures thereof Preferred couplers include resorcinol, 1-naphthol, 2-methylresorcinol, 4-amino-2-hydroxy toluene, m-aminophenol, 2,4-diaminophenoxyethanol, phenyl methyl pyrazolone, their salts, or mixtures.

In the haircolor industry, haircolor is classified into one of ten levels as follows:

| | |
|---|---|
| 1 = very black | 6 = light brown |
| 2 = bright black | 7 = dark blonde |
| 3 = very dark brown | 8 = medium blonde |
| 4 = dark brown | 9 = light blonde |
| 5 = medium brown | 10 = high lift blonde |

Set forth in the table below is a non-limiting example of the primary intermediates and the color couplers that may be used in various shades of hair color. Other primary intermediates and couplers may be used in addition to, or in lieu of, those set forth in the Table and nothing herein shall be construed to limit the invention to only those primary intermediates and couplers set forth.

| Primary Intermediates | Couplers |
|---|---|
| Level 1 - Very Black | |
| p-phenylenediamine | m-aminophenol |
| p-phenylenediamine | resorcinol |

-continued

| Primary Intermediates | Couplers |
| --- | --- |
| sulfate | |
| 2-chloro-phenylene diamine sulfate | 4-amino-2-hydroxy toluene |
| p-aminophenol | 4-chlororesorcinol |
| o-aminophenol | m-aminophenol HCL |
| | 2,4-diaminophenoxy ethanol |
| | m-phenylenediamine sulfate |
| Level 2 - Bright Black | |
| p-phenylenediamine | resorcinol |
| 2-chloro-P-phenylene-diamine sulfate | |
| o-aminophenol | |
| Level 3 - Very Dark Brown | |
| p-phenylenediamine | resorcinol |
| N,N-bis(2-hydroxy-ethyl)-P-phenylene-diamine sulfate | 1-naphthol |
| | m-aminophenol |
| Level 4 - Dark Brown | |
| p-phenylenediamine | resorcinol |
| N,N-bis(2-hydroxyethyl)-P-phenylene diamine sulfate | 1-naphthol |
| p-aminophenol | m-aminophenol |
| | phenyl methyl pyrazolone |
| o-aminophenol | 4-amino-2-hydroxytoluene |
| Level 5 - Medium Brown | |
| p-phenylenediamine | resorcinol |
| N,N-bis(2-hydroxy-ethyl)-P-phenylene diamine sulfate | 1-naphthol |
| p-aminophenol | m-aminophenol |
| o-aminophenol | phenyl methyl pyrazolone |
| | 2-methylresorcinol |
| | 4-amino-2-hydrox-toluene |
| Level 6 - Light Brown | |
| p-phenylenediamine | resorcinol |
| N,N-bis(2-hydroxy-ethyl)-P-phenylene diamine sulfate | 1-naphthol |
| p-aminophenol | m-aminophenol |
| | phenyl methyl pyrazolone |
| | 4-amino-2-hydroxy toluene |
| | 2-methylresorcinol |
| Level 7 - Dark Blonde | |
| p-phenylenediamine | resorcinol |
| N,N-bis(2-hydroxy-ethyl)-P-phenylene diamine sulfate | 1-naphthol |
| p-aminophenol | phenyl methyl pyrazolone |
| o-aminophenol | |
| Level 8 - Medium Blonde | |
| p-phenylenediamine | resorcinol |
| N,N-bis(2-hydroxyethyl)-P-phenylenediamine sulfate | 1-naphthol |
| p-aminophenol | m-aminophenol |
| | phenyl methyl pyrazolone |
| | 4-amino-2-hydroxytoluene |
| Level 9 - Light Blonde | |
| p-phenylenediamine | resorcinol |
| N,N-bis(2-hydroxyethyl)-P-phenylenediamine sulfate | 4-amino-2-hydroxy toluene |
| p-aminophenol | phenyl methyl pyrazolone |
| o-aminophenol | 2-methylresorcinol |
| | 1-naphthol |
| Level 10 - High Lift Blonde | |
| p-phenylenediamine | resorcinol |
| N,N-bis(2-hydroxy-ethyl)-P-phenylene-diamine sulfate | 1-naphthol |
| | phenyl methyl pyrazolone |
| | 2-methylresorcinol |

3. Alkalizing Agent

The dye mixture contains one or more alkalizing agents preferably in a range of about 1–5% based on the total weight of the dye mixture. The term "alkalizing agent" means an ingredient that is capable of imparting alkalinity (e.g. a pH of greater than 7) to the dye mixture. Suitable alkalizing agents include ammonium hydroxide, metal hydroxides, alkanolamines, sodium silicate, metal carbonates, sodium metasilicate, and mixtures thereof. Suitable metal hydroxides and carbonates include alkali metal and alkaline earth metal hydroxides or carbonates. Examples of such metal hydroxides include sodium, potassium, lithium, calcium, magnesium and so on. A particularly preferred alkaline earth metal hydroxide is sodium hydroxide. Suitable alkanolamines include mono-, di-, and trialkanolamines such as monoethanolamine (MEA), diethanolamine (DEA), triethanolamine (TEA), 2-aminobutanol, aminoethyl propanediol, aminomethyl propanediol, bis-hydroxyethyl tromethamine, diethanolamine, diethyl ethanolamine, diisopropanolamine, dimethylamino methylpropanol, dimethyl MEA, isopropanolamine, methylethanolamine, mixed isopropanolamines, triisopropanolamine, tromethamine, and mixtures thereof A particularly preferred alkanolamine is MEA.

The alkalizing agent present in the hair dye mixture may react with other ingredients in the mixture in situ, such as fatty acids, proteins or hydrolyzed proteins, and the like. Depending on the amount of alkalizing agent present and the presence or absence of ingredients that will react with the alkalizing agent, it is possible that the alkalizing agent may be completely reacted in situ, partially reacted in situ, or not reacted at all if there are no other ingredients in the composition that will react with the alkalizing agent. In the compositions and method of the invention, there must be a certain minimum level of free alkalinity or unreacted alkalizing agent present to achieve the desired results. In particular, the aqueous hair color composition that results after combining the hair dye mixture and the developer mixture must contain about 0.20 to 0.75 meq/gram of free alkalizing agent or free alkalinity concentration. In other words, in the aqueous hair color composition, the amount of alkalizing agent that remains free or unreacted with any fatty acids, hydrolyzed proteins, or other ingredients in the composition must range from about 0.20 to 0.75 meq/gram.

Most preferred are dye mixtures that contain ammonium hydroxide in combination with a second alkalizing agent such as an alkanolamine. In general, the amount of alkalizing agent found in the dye mixture will depend on the color of the dye. Less alkalizing agent is used with darker hair colors in Levels 1–6, whereas more alkalizing agent is necessary in lighter shades having Levels 7–10.

In the preferred embodiment of the invention, the alkalizing agent used is ammonium hydroxide, and the amount of ammonium hydroxide used in the dye mixtures of the invention are as follows, with all amounts set forth in meq/gram composition of dye mixture+developer mixture in "Amount as Applied", and the total composition of dye mixture in "Amount in Dye".

|  | Amount as Applied[1] Range meq/gram | Amount in Dye Mixture[2] Range meq/g |
|---|---|---|
| Level 1, 2: | 0.20–0.34 | 0.50–0.85 |
| Level 3, 4: | 0.34–0.52 | 0.85–1.3 |
| Level 5–9: | 0.52–0.64 | 1.3–1.6 |
| Level 10 | 0.64–0.75 | 1.6–1.88 |

[1]Amount as Applied means the amount of ammonium hydroxide in the composition obtained by combining 1 part of the hair dye mixture and 1.5 parts of the developer mixture.
[2]Amount in Dye means the amount of ammonium hydroxide in the hair dye mixture.

In the most preferred embodiment of the invention the hair dye mixture contains ammonium hydroxide (in the amounts set forth above) in addition to a second alkalizing agent selected from sodium hydroxide, alkanolamine, or metal hydroxide. Preferably the second alkalizing agent is an alkanolamine. The second alkalizing agent should not present in an amount at more than 20% in excess of the amount stoichiometrically required to neutralize the entire content of ingredients present in the dye mixture that are reactive with the second alkalizing agent (such as fatty acids, proteins, etc.). When reactive ingredients are fatty acids, the stoichiometric amounts of total fatty acid and second alkalizing agent can be determined by simply ascertaining the moles of total fatty acid present in the composition and the moles of alkalizing agent and determining the excess, if any. For example, the stoichiometric relationship between the fatty acid and an alkalizing agent which is monoethanolamine (as exemplified in the dye composition of Example 1) is calculated as follows:

| Compound | MW | Grams in Composition | Moles in composition |
|---|---|---|---|
| Oleic acid (fatty acid) | 282.5 | 12.5 | 0.044 |
| Monoethanolamine (second alkalizing agent) | 61.08 | 3.0 | 0.049 |
| Stoichiometric Excess of MEA | 11% | | |

Preferably, the stoichiometric excess of ingredient reactive with the entire fatty acid content of the mixture to form soap should range from 0 to 20%, more preferably 5–15%. Most preferred is where the dye mixture is prepared with all of the ingredients except the ammonium hydroxide and the reaction between the second alkalizing agent and the fatty acids and other reactive ingredients present is promoted by heating the mixture to a slightly elevated temperature. When most or all of the second alkalizing agent has reacted with the fatty acids and other ingredients present, the mixture is cooled to room temperature and the ammonium hydroxide is added. Since the second alkalizing agent has already reacted with the reactive ingredients present, there are no such remaining ingredients to react with the ammonium hydroxide. As a result, the ammonium hydroxide remains free in the composition, e.g. "free alkalinity" and then acts to swell the hair shaft to facilitate permeation of the shaft by the dye molecules and hydrogen peroxide.

4. Other Ingredients (a) Fatty Acids

The dye mixture may contain one or more fatty acids, and if so suggested ranges are about 0.001–15%, preferably 0.005–10%, most preferably 0.01–8% by weight of the total composition. If fatty acids are present they will react with the alkalizing agent to form soap in situ, which provides a more shampoo-like character to the aqueous hair color composition once it is applied to hair. Such fatty acids are of the general formula RCOOH wherein R is a straight or branched chain, saturated or unsaturated $C_{6-30}$ alkyl. Examples of suitable fatty acids include oleic acid, stearic acid, myristic acid, linoleic acid, and so on. Particularly preferred is oleic acid.

(b) Conditioners

Preferably the dye mixture comprises one or more conditioners that exert a conditioning effect on hair. A variety of conditioners are suitable including cationic polymers, oily conditioning agents, fatty alcohols, proteins, and so on. A combined total weight of conditioners ranges from about 0.1–25%, preferably 0.5–20%, more preferably 1–15% by weight of the total composition.

(i) Cationic Polymers

A variety of cationic polymers are suitable such as quaternary derivatives of cellulose ethers or guar derivatives, copolymers of vinylpyrrolidone, polymers of dimethyldiallyl ammonium chloride, acrylic or methacrylic polymers, quaternary ammonium polymers, and the like.

(aa) Quaternary Derivatives of Cellulose

Examples of quaternary derivatives of cellulose ethers are polymers sold under the tradename JR-125, JR-400, JR-30M. Suitable guar derivatives include guar hydroxypropyl trimonium chloride.

(bb) Copolymers of Vinylpyrrolidone

Copolymers of vinylpyrrolidone having monomer units of the formula:

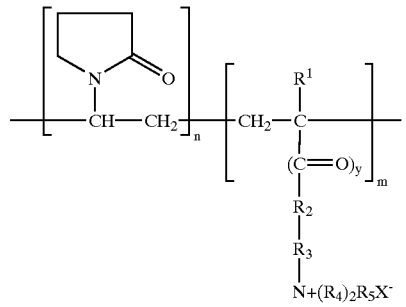

wherein $R^1$ is hydrogen or methyl, preferably methyl;
y is 0 or 1, preferably 1
$R^2$ is O or NH, preferably NH;
$R^3$ is $C_xH_{2x}$ where x is 2 to 18, or —$CH_2$—CHOH—$CH_2$, preferably $C_xH_{2x}$ where x is 2;
$R^4$ is methyl, ethyl, phenyl, or $C_{1-4}$ substituted phenyl, preferably methyl; and $R^5$ is methyl or ethyl, preferably methyl.

(cc) Polymers of Dimethyldiallylammonium Chloride

Homopolymers of dimethyldiallylammonium chloride, or copolymers of dimethyldiallylammonium chloride and acrylamide are also suitable. Such compounds are sold under the tradename MERQUAT by Calgon.

(dd) Acrylic or Methacrylic Acid Polymers

Homopolymers or copolymers derived from acrylic or methacrylic acid, selected from monomer units acrylamide, methylacrylamide, diacetone-acrylamide, acrylamide or methacrylamide substituted on the nitrogen by lower alkyl, alkyl esters of acrylic acid and methacrylic acid, vinylpyrrolidone, or vinyl esters are suitable for use.

(ee) Polymeric Quaternary Ammonium Salts

Also suitable are polymeric quaternary ammonium polymers such as Polyquaternium 10, 28 31, 33, 34, 35, 36, 37, and 39.

(ff) Diquaternary Polydimethylsiloxanes

Also suitable are diquaternary polydimethylsiloxanes such as Quaternium-80, sold by Goldschmidt Corporation under the tradename ABIL-Quat 3272.

Examples of other cationic polymers that can be used in the compositions of the invention are disclosed in U.S. Pat. Nos. 5,240,450 and 5,573,709, which are hereby incorporated by reference.

Particularly preferred are conditioners Polyquaternium 10 and Polyquaternium 28. Polyquaternium–10 is the polymeric quaternary ammonium salt of hydroxyethyl cellulose reacted with trimethyl ammonium substituted epoxide. Polyquaternium-28 is the polymeric quaternary ammonium salt consisting of vinyl pyrrolidone and dimethylaminopropyl methacrylamide monomers.

(gg) Oily Conditioning Agents

Also suitable are a variety of oily materials that provide good conditioning effect to hair. Suitable oils are liquid at room temperature and may comprise esters, hydrocarbons, and the like. Preferably the composition comprises 0.001–20%, more preferably 0.005–15%, most preferably 0.01–10% by weight of the total composition of such oils. Particularly preferred oily conditioning agents are oils extracted from vegetable sources, specifically meadowfoam seed oil.

(hh) Nonionic Silicones

Also suitable as conditioning agents are one or more silicones. Suitable silicone hair conditioning agents include volatile or nonvolatile nonionic silicone fluids, silicone resins, and silicone semi-solids or solids.

Volatile silicones are linear or cyclic silicones having a measureable vapor pressure, which is defined as a vapor pressure of at least 2 mm. of mercury at 20° C. Examples of volatile silicones are cyclic silicones having the general formula:

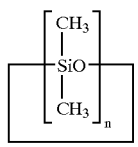

where n=3–7.

Also, linear volatile silicones that may be used in the compositions of the invention have the general formula:

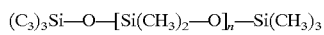

where n=0–7, preferably 0–5.

The silicone hair conditioning agent may comprise water insoluble nonvolatile silicone fluids including polyalkyl siloxanes, polyaryl siloxanes, polyalkylaryl siloxanes, polyether siloxane copolymers, amine-functional silicones, and mixtures thereof Such silicones have the following general formula:

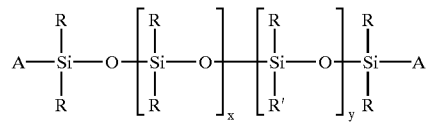

wherein R and R' are each independently alkyl, aryl, or an alkyl substituted with one or more amino groups, and x and y are each independently 0–100,000, with the proviso that x+y equals at least one and A is siloxy endcap unit. Preferred is where A is methyl, R is methyl, and R' is an alkyl substituted with at least two amino groups, most preferably an amine-functional silicone having the formula:

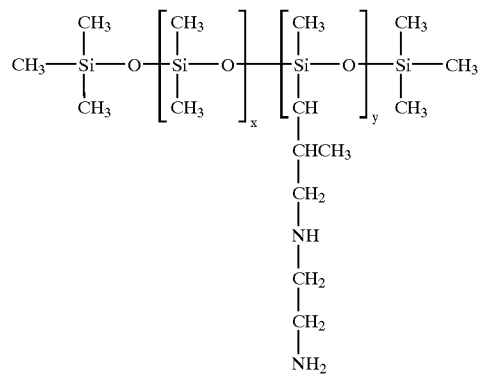

which is known by the CTFA name trimethylsilylamodimethicone.

The silicone hair conditioning agent may also be a silicone polymer having the following general formula:

wherein R, R' and R" are each independently a $C_{1-10}$ straight or branched chain alkyl or phenyl, and x and y are such that the ratio of $(RR'R'')_3SiO_{1/2}$ units to $SiO_2$ units is 0.5 to 1 to 1.5 to 1.

Preferably R, R' and R" are a $C_{1-6}$ alkyl, and more preferably are methyl and x and y are such that the ratio of $(CH_3)_3SiO_{1/2}$ units to $SiO_2$ units is 0.75 to 1. Most preferred is this trimethylsiloxy silicate containing 2.4 to 2.9 weight percent hydroxyl groups which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 2–0749 and 2–0747, each of which is a blend of about 40–60% volatile silicone and 40–60% trimethylsiloxy silicate. Dow Corning 2–0749, in particular, is a fluid containing about 50% trimethylsiloxy silicate and about 50% cyclomethicone. The fluid has a viscosity of 200–700 centipoise at 25° C., a specific gravity of 1.00 to 1.10 at 25° C., and a refractive index of 1.40–1.41.

Preferably the developer composition contains a mixture of 0.001–10%, preferably 0.005–5, more preferably 0.01–4%, of each of cyclomethicone, trimethylsiloxysilicate, and a water insoluble nonvolatile silicone, in particular trimethylsilylamodimethicone.

(c) Surfactants or Emulsifiers

The dye composition of the invention preferably comprises one or more surfactants that assist in maintaining the composition in the preferred emulsion form and aid in the foaming capability of the composition. Suitable surfactants include anionic surfactants, nonionic surfactants, amphoteric surfactants, and the like.

(i) Nonionic Surfactants

Suggested ranges of nonionic surfactant are about 0.01–10%, preferably about 0.05–8%, more preferably about 0.1–7% by weight of the total composition. Suitable nonionic surfactants include alkoxylated alcohols or ethers, alkoxylated carboxylic acids, sorbitan derivatives, and the like.

Suitable alkoxylated alcohols, or ethers, are formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include steareth 2–30, which is formed by the reaction of stearyl alcohol and ethylene oxide where the number of repeating ethylene oxide units is 2 to 30; Oleth 2–30 which is formed by the reaction of oleyl alcohol and ethylene oxide where the number of repeating ethylene oxide units is 2 to 30; Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, and so on. Particularly preferred are Steareth-21, which is the reaction product of a mixture of stearyl alcohol with ethylene oxide, and the number of repeating ethylene oxide units in the molecule is 21, and Oleth-20 which is the reaction product of oleyl alcohol and ethylene oxide wherein the number of repeating ethylene oxide units in the molecule is 20.

Also suitable as the nonionic surfactant are alkyoxylated carboxylic acids, which are formed by the reaction of a carboxylic acid with an alkylene oxide or with a polymeric ether. The resulting products have the general formula:

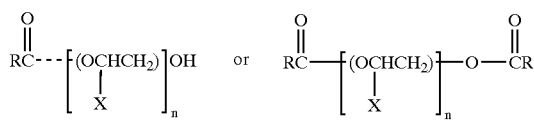

where RCO is the carboxylic ester radical, X is hydrogen or lower alkyl, and n is the number of polymerized alkoxy groups. In the case of the diesters, the two RCO-groups do not need to be identical. Preferably, R is a $C_{6-30}$ straight or branched chain, saturated or unsaturated alkyl, and n is from 1–100.

Also suitable are various types of alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate sorbitan stearate, and so on.

(ii) Anionic Surfactants

If desired the dye composition may contain one or more anionic surfactants. Together with the soap formed by the reaction of the fatty acid and alkanolamine or metal hydroxide, the ingredients provide the composition with the characteristics of shampoo. Preferred ranges of anionic surfactant are about 0.1–25%, preferably 0.5–20%, more preferably 1–15% by weight of the total composition. Suitable anionic surfactants include alkyl and alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula:

wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide. The fatty acids may be derived from coconut oil, for example.

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula:

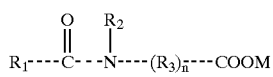

wherein $R_1$ is a $C_{8-24}$ alkyl or alkenyl radical, preferably $C_{10-18}$; $R_2$ is H, $C_{1-4}$ alkyl, phenyl, or $—CH_2COOM$; $R_3$ is $CX_2—$ or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

Also suitable are amphoteric and zwitterionic surfactants. Examples of amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

(d) Thickening Agents

Preferably the dye composition contains one or more thickening agents that increase the viscosity of the composition such that when it is applied to hair it doesn't run. The amount of thickening agent if present is about 0.001–5%, preferably about 0.005–4%, more preferably about 0.005–3% by weight of the total composition.

A variety of thickening agents are suitable including low melting point waxes, carboxyvinyl polymers, and the like. Particularly preferred thickening agents are low melting point waxes such as emulsifying wax, fatty alcohols (e.g. stearyl alcohol, cetearyl alcohol, behenyl alcohol, and the like). Preferred are cetearyl alcohol and emulsifying wax.

(e) Solvents

It may be desirable to include one or more solvents in the dye composition. Such solvents assist in solubilizing the primary intermediate dyestuff and coupler dyestuff components, in addition to the other ingredients in the composition. The solvent is preferably present at about 0.01–10%, preferably 0.05–8%, more preferably 0.1–7% by weight of the total composition. Suitable solvents include $C_{2-4}$ alkanols such as ethanol, isopropanol, propanol, etc., as well as askoxydiglycols such as ethoxydiglycol. The preferred solvent comprises ethoxydiglycol.

(f) Chelating Agents

Preferably, the dye mixture contains one or more chelating agents that are capable of chelating the metal ions found in water. If water contains too many extraneous metal ions they can interfere with the coloration process. Preferred ranges of chelating agent are 0.001–5%, preferably 0.005–4%, more preferably 0.01–3% by weight of the total composition. Preferred chelating agents are EDTA, HEDTA, and sodium or potassium salts thereof.

(g) Antioxidants

The dye mixture may also contain one or more antioxidants as described herein with respect to the dye composition and in the same ranges by weight.

Various other ingredients such as preservatives may also be incorporated into the claimed compositions.

A. The Developer Mixture

The developer mixture in its simplest form is an aqueous solution of hydrogen peroxide. Preferably the developer composition comprises 1–99%, preferably 10–99%, more preferably 60–97% of water, and about 5–20%, preferably 6–15%, more preferably 7–10% by weight of the total developer composition of hydrogen peroxide. Developer compositions are generally sold in the form of 10, 20, 25, and 30 volume hydrogen peroxide. The 25 volume hydrogen peroxide developer composition contains about 7.5% by weight of the total composition of hydrogen peroxide. The 30 volume hydrogen peroxide developer composition contains about 9% by weight of the total composition of hydrogen peroxide. If desired, the developer composition may contain a variety of other ingredients that enhance the aesthetic properties and contribute to more efficient coloring of hair. Preferred developer compositions comprise:

0.5–25% hydrogen peroxide,
0.1–10% of a conditioner,
0.01–5% of a thickener, and
1–99% water.

1. Conditioners

The developer composition may contain one or more conditioners that exert a conditioning effect on hair. The conditioners mentioned in Section 4(c) above are also suitable for use in the developer composition, and in the same suggested ranges. Also suitable are various types of cationic silicones.

(a) Cationic Silicones

As used herein, the term "cationic silicone" means any silicone polymer or oligomer having a silicon backbone, including polysiloxanes, having a positive charge on the silicone structure itself. Cationic silicones that may be used in the compositions of the invention include those corresponding to the following formula, where the ratio of D to T units, if present, are greater than about 80 D units to 1 T unit:

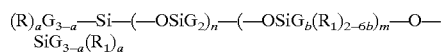

in which G is selected from the group consisting of H, phenyl, OH, $C_{1-10}$ alkyl, and is preferably $CH_3$; and a is 0 or an integer from 1 to 3, and is preferably 0; b is 0 or 1, preferably 1; the sum n+m is a number from 1 to 2,000 and is preferably 50 to 150; n is a number from 0 to 2000, and is preferably 50 to 150; and m is an integer from 1 to 2000, and is preferably 1 to 10; R is a $C_{1-10}$ alkyl, and $R_1$ is a monovalent radical of the formula $C_qH_{2q}L$ in which q is an integer from 2 to 8 and L is selected from the groups:

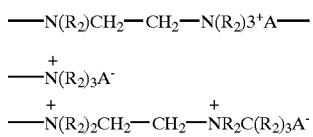

in which $R_2$ is selected from the group consisting of H, phenyl, benzyl, a saturated hydrocarbon radical, and is preferably an alkyl radical containing 1–20 carbon atoms; and A- is a halide, methylsulfate, or tosylate ion.

2. Thickeners

The developer composition may contain one or more thickeners that assist in maintaining an increased viscosity of the final composition resulting from mixture of the hair dye and the developer compositions. This ensures that the mixture is of a sufficient viscosity to prevent it from dripping or running off the hair onto the user's face or the surrounding environment. Suitable thickeners are those set forth in Section 4(e) above and in the same ranges. Also suitable are a variety of water soluble anionic thickening polymers such as those disclosed in U.S. Pat. No. 4,240,450, which is hereby incorporated by reference. Suggested ranges of such polymers are about 0.01–5%, preferably 0.05–4%, more preferably 0.1–3% by weight of the total developer composition. Examples of such anionic polymers are copolymers of vinyl acetate and crotonic acid, graft copolymers of vinyl esters or acrylic or methacrylic acid esters, cross-linked graft copolymers resulting from the polymerization of at least one monomer of the ionic type, at least one monomer of the nonionic type, polyethylene glycol, and a crosslinking agent, and the like. Preferred are acrylate copolymers such as steareth-10 allyl ether acrylate copolymer.

3. Other Ingredients (a). Nonionic Surfactants

The developer composition may contain one or more nonionic surfactants which assist in maintaining the composition in stable emulsion form. Suitable nonionic surfactants are the same as those mentioned in Section 4(d)(i) and in the same amounts.

(b). Chelating Agents

The developer composition may contain one or more chelating agents as described herein with respect to the dye composition, and in the same ranges by weight.

II. Combining the Dye Mixture and Hydrogen Peroxide Mixture

The hair dye mixture and hydrogen peroxide mixture are combined immediately prior to use to form the aqueous hair color composition. The dye mixture and the developer mixture may be combined in any proportions so long as the aqueous hair dye mixture that is applied to the hair comprises:

a) 0.01–2.0% (combined weight) of the total composition of primary intermediates and couplers, b) a free alkalinity concentration of 0.20–0.75 meq/gram, and c) a hydrogen peroxide concentration of 4–6%, preferably 4.6 to 5.5% by weight of the total composition.

The preferred amount of hydrogen peroxide actually applied to the hair may be further broken down according to the Level of color provided by the aqueous haircolor composition as set forth in the table below:

| Levels | Exact % | % Range |
| --- | --- | --- |
| 1–9 | 4.5 | 4.5–5.5 |
| 10 | 5.40 | 5–6 |

The amount of free alkalinity in the aqueous hair color composition that is applied to the air is set forth on the table below with the amounts set forth in meq/gram:

| | Range |
| --- | --- |
| Level 1, 2: | 0.2–0.34 |
| Level 3, 4: | 0.34–0.52 |
| Level 5–9: | 0.53–0.64 |
| Level 10 | 0.64–0.75 |

The term "free alkalinity" or "free alkalizing agent" means the portion of alkalizing agent that has not reacted with the fatty acids or any other ingredients in the composition and, as such, remains free to swell the hair shaft and promote penetration of the dyes and hydrogen peroxide into the shaft.

The amount of primary intermediates and couplers (combined) in the aqueous hair color composition applied to the hair is set forth below:

| Level | Combined primary Intermediates and Couplers (wt %) |
| --- | --- |
| 1 | 0.9–1.9 |
| 2 | 0.8–1.8 |
| 3 | 0.7–1.7 |
| 4 | 0.6–1.6 |
| 5 | 0.5–1.5 |
| 6 | 0.4–1.2 |
| 7 | 0.3–1.0 |
| 8 | 0.2–0.8 |
| 9 | 0.1–0.6 |
| 10 | 0.01–0.3 |

In the preferred embodiment of the invention, about 1 part of dye mixture is combined with 1.5 parts of the developer mixture to form the aqueous hair color composition. This combination is then immediately applied to hair and allowed to remain for twelve, preferably ten minutes. After ten minutes the hair is rinsed thoroughly with water. The hair colored according to this method and with such compositions is fully colored at least by ten minutes, which is a substantial improvement over currently existing compositions. Since the process both lifts and colors the hair, it is possible to color the hair in whatever color is desired without restriction.

II. The Hair Color Kit

The invention is also directed to a hair coloring kit containing separate containers of I. an aqueous dye mixture comprising:

a) primary intermediates and color couplers, and b) ammonium hydroxide; and

II. an aqueous hydrogen peroxide developing mixture;

wherein when the aqueous hair dye mixture is combined with the aqueous developing mixture, the composition that is applied to the hair comprises:

a) 0.01–2.0% (combined weight) of the total composition of primary intermediates and couplers, b) a free ammonia concentration of 0.20–0.75 meq/gram, and c) a hydrogen peroxide concentration of 4.0–6.0% by weight of the total composition.

The hair dye composition and the developing composition are as described above. The hair dye composition may be stored in glass bottles or metal or plastic tubes, while the developer composition is most often found in plastic bottles. Immediately prior to coloring the hair, the dye mixture found in the bottle or tube is combined with the developer by pouring or squeezing the contents into the plastic container that contains the developer mixture. The two compositions are mixed well. The contents of the plastic bottle are then applied to hair and shampooed in, ensuring that the color permeates all the hair. This mixture is left on the hair for at least 10 minutes and rinsed off with water. The resulting haircolor provides the same degree of color found with traditional hair colors but in substantially less time.

The invention will be further described in connection with the following examples which are set forth for the purposes of illustration only.

EXAMPLE 1

A hair dye mixture in the level 5, medium brown, shade was prepared according to the following formula:

| | w/w % |
| --- | --- |
| P-phenylenediamine | 0.63 (primary intermediate) |
| N,N-bis (2-hydroxyethyl)-P-phenylene diamine sulfate | 0.11 (primary intermediate) |
| Resorcinol | 0.50 (coupler) |
| 1-naphthol | 0.04 (coupler) |
| M-aminophenol | 0.07 (coupler) |
| Ethanolamine | 3.00 (alkalizing agent) |
| Ammonium hydroxide (27.5%) | 9.00 (alkalizing agent) |
| Oleic acid | 12.50 (fatty acid) |
| Erythorbic acid | 0.20 (antioxidant) |
| Sodium sulfite | 0.50 (antioxidant) |
| Ethoxydiglycol | 5.00 (solvent) |
| Hypnea musciformis extract, gellidiela acerosa extract, sargassum filipendula extract, sorbitol | 0.80 (conditioner) |
| Oleth-20 | 1.00 (emulsifier) |

-continued

| | w/w % |
|---|---|
| Steareth-21 | 0.70 (emulsifier) |
| Emulsifying wax | 2.00 (thickener, emulsifier) |
| Meadowfoam seed oil | 0.75 (conditioner) |
| Polyquaternium-10 | 0.20 (conditioner) |
| Polyquaternium-28 | 0.50 (conditioner) |
| Hydrolyzed wheat protein | 0.50 (conditioner) |
| Oleyl alcohol | 0.40 (conditioner, thickener) |
| Cetearyl alcohol | 4.00 (thickener) |
| Tetrasodium EDTA (38%) | 0.80 (chelating agent) |
| Ammonium lauryl sulfate (28%) | 2.00 (anionic surfactant) |
| Mica, titanium dioxide (67:33) | 0.30 (pigments) |
| Sodium benzotriaolyl butylphenol sulfonate buteth-3, tributyl citrate | 0.50 (UV absorber) |
| Fragrance | 1.25 |
| Water | 52.75 |

The composition was prepared by combining all the ingredients except the ammonium hydroxide and fragrance mixing well to emulsify while heating to a temperature of about 25 to 80° C. The mixture was then cooled to room temperature and the ammonium hydroxide and fragrance were added with mixing. The composition was stored in a tube of laminated plastic and metal.

EXAMPLE 2

A developer composition was prepared according to the following formula:

| | w/w % |
|---|---|
| Water | 69.72 |
| Methylparaben | 0.05 |
| EDTA | 0.02 |
| Mineral oil | 0.60 |
| Cetearyl alcohol/ceteareth-20 (80:20) | 3.75 |
| Cetearyl alcohol | 0.80 |
| Ceteareth-20 | 0.40 |
| Cyclomethicone/trimethylsiloxysilicate (50:50) | 0.01 |
| Trimethylsilylamodimethicone, C11–15 pareth-7 C12–16 pareth 9, trideceth-12, glycerin, water (20:6:4:2:3:65) | 2.00 |
| Disodium phosphate | 0.03 |
| Phosphoric acid | 0.02 |
| Hydrogen peroxide (35%) | 22.50 |
| Steareth-10 allyl ether/acrylates copolymer | 0.10 |

The composition was prepared by combining all ingredients and mixing well. The composition was stored in a plastic container.

EXAMPLE 3

The compositions of Examples 1 and 2 were compared with Revlon Colorstay haircolor level 5, medium brown; and L'Oreal Preference haircolor, level 5, medium brown to ascertain the rate of color formation, ΔE which was calculated according to the following formula:

$$\Delta E = \sqrt{(L-L_o)^2 + (a-a_o)^2 + (b-b_o)^2}$$

wherein L is the is the level of darkness or lightness, a is the red and green components, and b is yellow and blue components, and wherein the subscript o means prior to dyeing. All of L, a, and b, were measured using a DataColor calorimeter.

One part of the hair dye mixture of Example 1 was combined with 1.5 parts of the developer composition of claim 2 and applied to a group of 95% gray hair swatches. The dye process was halted at 2 minutes for one group of swatches, 5 minutes for the second group of swatches, 10 minutes for the third group of swatches, 25 minutes for the fourth group of swatches and 42 minutes for the fifth group of swatches. In the same manner the groups of 95% gray hair swatches were dyed using Revlon Colorstay haircolor and L'Oreal Preference haircolor according to the directions enclosed with each package and the dye process was halted at 2, 5, 10, 25, and 42 minutes for different groups of swatches. The L, a, and b values were measured on all the hair swatches using the DataColor Colorimeter. The results are set forth below:

| Invention | | | | | L'Oreal Preference | | | | | Revlon Colorstay | | | | |
|---|---|---|---|---|---|---|---|---|---|---|---|---|---|---|
| time | L | a | b | ΔE | time | L | a | b | ΔE | time | L | a | b | ΔE |
| 0 | 58.06 | 0.88 | 15.08 | 0.00 | 0 | 59.09 | 0.84 | 14.8 | 0.00 | 0 | 58.06 | 0.88 | 15.1 | 0.00 |
| 2 | 44.01 | 2.65 | 7.8 | 15.93 | 2 | 49.38 | 1.54 | 10.35 | 10.71 | 2 | 46.2 | 1.82 | 8.51 | 13.59 |
| 5 | 33.61 | 3.75 | 8.25 | 25.55 | 5 | 43.88 | 2.11 | 7.96 | 16.73 | 5 | 36.08 | 2.74 | 7.4 | 23.36 |
| 10 | 29.86 | 3.71 | 8.13 | 29.18 | 10 | 38.02 | 2.3 | 8.21 | 22.13 | 10 | 31.55 | 3.01 | 7.85 | 27.56 |
| 25 | 21.42 | 3.5 | 5.85 | 37.87 | 25 | 26.91 | 2.49 | 6.6 | 33.25 | 25 | 25.37 | 3.15 | 7.13 | 33.72 |
| 42 | 18.44 | 2.99 | 4.57 | 41.35 | 42 | 23.8 | 2.61 | 6.64 | 36.27 | 42 | 20.31 | 2.83 | 4.75 | 39.19 |

(The standard deviation of the measurements is estimated to be about +/−0.05). The above results illustrate that when the dye composition of the invention is combined with the hydrogen peroxide composition as described above, the ΔE at 2, 5, 10, 25, and 42 minutes for the compositions of the invention is significantly greater than the ΔE for Revlon Colorstay and L'Oreal Preference at the same time intervals. Thus, the claimed dye composition is capable of depositing more color on the hair in a shorter time period than the Revlon Colorstay and L'Oreal Preference products.

EXAMPLE 4

A test similar to that set forth in Example 3 was conducted with the composition of the invention, Revlon Colorstay and L'Oreal Feria all in the color medium golden brown level 5. As described in Example 3, groups of 95% gray hair swatches were colored with a dye composition of the invention by mixing 1 part of the dye composition and 1.5 parts of the hydrogen peroxide composition of Example 2. This mixture was applied to groups of hair swatches and the coloring process was interrupted at 2, 5, 10, 25, and 42 minutes. Similarly, 95% gray hair swatches were colored with L'Oreal Feria and Revlon Colorstay using the directions set forth in the package insert in the same manner by stopping the color process at 2, 5, 10, 25, and 42 minutes. The following results were obtained:

|  | Invention | | | | L'Oreal Feria | | | | Revlon Colorstay | | | |
| --- | --- | --- | --- | --- | --- | --- | --- | --- | --- | --- | --- | --- |
| time | L | a | b | ΔE | time | L | a | b | ΔE | time | L | a | b | ΔE |
| 0 | 58.47 | 0.76 | 15.34 | 0.00 | 0 | 58.47 | 0.76 | 15.34 | 0.00 | 0 | 57.41 | 0.88 | 14.6 | 0 |
| 2 | 42.65 | 4.88 | 11.73 | 16.74 | 2 | 52.35 | 3 | 14.6 | 6.56 | 2 | 48.33 | 3.04 | 9.94 | 11.71 |
| 5 | 31.66 | 6.71 | 11.26 | 27.76 | 5 | 43.78 | 4.09 | 12.17 | 15.39 | 5 | 37.01 | 4.98 | 10.5 | 22.41 |
| 10 | 24.61 | 6.51 | 11.22 | 34.59 | 10 | 36.43 | 5.06 | 12.56 | 22.63 | 10 | 30.3 | 5.64 | 11.3 | 29.14 |
| 25 | 20.07 | 5.23 | 6.09 | 39.75 | 25 | 26.24 | 5.23 | 9.68 | 33.03 | 25 | 25.85 | 5.39 | 9.72 | 33.42 |
| 42 | 18.14 | 3.57 | 2.77 | 42.34 | 42 | 26.04 | 5.79 | 9.11 | 33.40 | 42 | 25.64 | 5.71 | 9.67 | 33.68 |

(The standard deviation of the above results is estimated to be about +/−0.05. The above results illustrate that when the dye composition of the invention in a medium brown shade is combined with the hydrogen peroxide composition as described above, the ΔE at 2, 5, 10, 25, and 42 minutes for the compositions of the invention is significantly greater than the ΔE for Revlon Colorstay and L'Oreal Preference at the same time intervals. Thus, the claimed dye composition is capable of depositing more color on the hair in a shorter period of time than the Revlon Colorstay and L'Oreal Feria products.

EXAMPLE 5

A test similar to that set forth in Examples 3 and 4 was conducted with the composition of the invention and L'Oreal Excellence, both in a Level 3 very dark brown. As described in Examples 3 and 4, groups of 95% gray hair swatches were colored with a dye composition of the invention by mixing 1 part of the dye composition and 1.5 parts of the hydrogen peroxide composition of Example 2. This mixture was applied to groups of hair swatches and the coloring process was interrupted at 2, 5, 10, 20, and 30 minutes. Similarly, 95% gray hair swatches were colored with L'Oreal Excellence using the directions set forth in the package insert in the same manner by stopping the color process at 2, 5, 10, 20, and 30 minutes. The following results were obtained (standard deviation estimated to be about +/−0.05):

|  | Invention | | | | L'Oreal Excellence | | | |
| --- | --- | --- | --- | --- | --- | --- | --- | --- |
| time | L | a | b | ΔE | time | L | a | b | ΔE |
| 0 | 61.08 | 1.86 | 14.35 | 0 | 0 | 61.08 | 1.86 | 14.35 | 0 |
| 2 | 37.64 | 3.80 | 6.10 | 24.93 | 2 | 50.22 | 2.06 | 7.28 | 12.96 |
| 5 | 26.98 | 3.56 | 4.58 | 35.51 | 5 | 34.63 | 3.55 | 8.15 | 27.22 |
| 10 | 22.34 | 2.70 | 2.92 | 40.40 | 10 | 22.45 | 3.13 | 5.48 | 39.66 |
| 20 | 18.28 | 1.30 | 0.61 | 44.95 | 20 | 18.89 | 2.12 | 2.67 | 43.78 |
| 30 | 16.40 | 1.93 | 1.16 | 46.59 | 30 | 18.73 | 1.89 | 2.12 | 44.08 |

The above results illustrate that when the dye composition of the invention in a Level 3 very dark brown shade is combined with the hydrogen peroxide composition as described above, the ΔE at 2, 5, 10, 20, and 30 minutes for the compositions of the invention is significantly greater than the ΔE for L'Oreal Excellence haircolor at the same time intervals. Thus, the claimed dye composition is capable of depositing more color on the hair in a faster time than the L'Oreal Excellence product.

EXAMPLE 6

A test similar to that set forth in Examples 3, 4, and 5 was conducted with the composition of the invention and L'Oreal Feria, both in a Level 2, bright black color. As described in Examples 3, 4, and 5, groups of 95% gray hair swatches were colored with a dye composition of the invention by mixing 1 part of the dye composition and 1.5 parts of the hydrogen peroxide composition of Example 2. This mixture was applied to groups of hair swatches and the coloring process was interrupted at 2, 5, and 10 minutes. Similarly, 95% gray hair swatches were colored with L'Oreal Feria using the directions set forth in the package insert in the same manner by stopping the color process at 2, 5, and 10 minutes. The following results were obtained (standard deviation estimated to be about +/−0.05):

|  | Invention | | | | L'Oreal Feria | | | |
| --- | --- | --- | --- | --- | --- | --- | --- | --- |
| time | L | a | b | ΔE | time | L | a | b | ΔE |
| 0 | 61.08 | 1.86 | 14.35 | 0 | 0 | 61.08 | 1.86 | 14.35 | 0 |
| 2 | 30.93 | 2.17 | −9.18 | 38.25 | 2 | 42.33 | −1.39 | −4.57 | 26.83 |
| 5 | 18.55 | 2.54 | −7.74 | 47.93 | 5 | 28.19 | 0.38 | −8.83 | 40.26 |
| 10 | 18.18 | 2.05 | −6.32 | 47.62 | 10 | 20.86 | 0.85 | −8.13 | 46.09 |

The above results illustrate that when the dye composition of the invention in a Level 2 bright black shade is combined with the hydrogen peroxide composition as described above, the ΔE at 2, 5, and 10 minutes for the compositions of the invention is significantly greater than the ΔE for L'Oreal Feria haircolor at the same time intervals. Thus, the claimed dye composition is capable of depositing more color on the hair in a shorter period of time than the L'Oreal Feria product.

EXAMPLE 7

A test similar to that set forth in Examples 3, 4, 5, and 6 was conducted with the composition of the invention and L'Oreal Feria, both in a Level 3, very dark brown. As described in Examples 3, 4, and 5, groups of 95% gray hair swatches were colored with a dye composition of the invention by mixing 1 part of the dye composition and 1.5 parts of the hydrogen peroxide composition of Example 2. This mixture was applied to groups of hair swatches and the coloring process was interrupted at 2, 5, and 10 minutes. Similarly, 95% gray hair swatches were colored with L'Oreal Feria using the directions set forth in the package insert in the same manner by stopping the color process at 2, 5, and 10 minutes. The following results were obtained (standard deviation estimated to be about +/−0.05):

| Invention | | | | L'Oreal Feria | | | |
|---|---|---|---|---|---|---|---|
| time | L | a | b | ΔE | time | L | a | b | ΔE |
| 0 | 61.08 | 1.86 | 14.35 | 0 | 0 | 61.08 | 1.86 | 14.35 | 0 |
| 2 | 25.42 | 5.29 | 2.04 | 37.88 | 2 | 32.68 | 8.3 | 7.76 | 29.86 |
| 5 | 19.81 | 4.55 | 1.3 | 43.37 | 5 | 24.77 | 7.03 | 5.42 | 37.75 |
| 10 | 16.52 | 2.47 | 0.47 | 46.68 | 10 | 21.79 | 6.42 | 4.3 | 40.81 |

The above results illustrate that when the dye composition of the invention in a Level 3 brown shade is combined with the hydrogen peroxide composition as described above, the ΔE at 2, 5, and 10 minutes for the compositions of the invention is significantly greater than the ΔE for L'Oreal Feria haircolor at the same time intervals. Thus, the claimed dye composition is capable of depositing more color on the hair in a shorter period of time than the L'Oreal Feria product.

EXAMPLE 8

A test similar to that set forth in Examples 3–6 was conducted with the composition of the invention and L'Oreal Feria, both in a Level 7 dark blonde shade. As described in Examples 3–6, groups of 95% gray hair swatches were colored with a dye composition of the invention by mixing 1 part of the dye composition and 1.5 parts of the hydrogen peroxide composition of Example 2. This mixture was applied to groups of hair swatches and the coloring process was interrupted at 2, 5, and 10 minutes. Similarly, 95% gray hair swatches were colored with L'Oreal Feria using the directions set forth in the package insert in the same manner by stopping the color process at 2, 5, and 10 minutes. The following results were obtained (standard deviation estimated to be about +/–0.05):

| Invention | | | | L'Oreal Feria | | | |
|---|---|---|---|---|---|---|---|
| time | L | a | b | ΔE | time | L | a | b | ΔE |
| 0 | 61.08 | 1.86 | 14.35 | 0 | 0 | 61.08 | 1.86 | 14.35 | 0 |
| 2 | 52.39 | 19.67 | 25.27 | 22.63 | 2 | 57.47 | 12.77 | 22.15 | 13.89 |
| 5 | 42.41 | 21.65 | 24 | 28.87 | 5 | 48.94 | 17.57 | 22.57 | 21.49 |
| 10 | 34.86 | 21.56 | 21.67 | 33.60 | 10 | 42.68 | 21.75 | 26.38 | 29.65 |

The above results illustrate that when the dye composition of the invention in a Level 7 dark blonde shade is combined with the hydrogen peroxide composition as described above, the ΔE at 2, 5, and 10 minutes for the compositions of the invention is significantly greater than the ΔE for L'Oreal Feria hair color at the same time intervals. Thus, the claimed dye composition is capable of depositing more color on the hair in a shorter period of time than the L'Oreal Feria product.

EXAMPLE 9

A test similar to that set forth in Examples 3–7 was conducted with the composition of the invention and L'Oreal Feria, both in a Level 8 medium blonde shade. As described in Examples 3–6, groups of 95% gray hair swatches were colored with a dye composition of the invention by mixing 1 part of the dye composition and 1.5 parts of the hydrogen peroxide composition of Example 2. This mixture was applied to groups of hair swatches and the coloring process was interrupted at 2, 5, and 10 minutes. Similarly, 95% gray hair swatches were colored with L'Oreal Feria using the directions set forth in the package insert in the same manner by stopping the color process at 2, 5, and 10 minutes. The following results were obtained:

| Invention | | | | L'Oreal Feria | | | |
|---|---|---|---|---|---|---|---|
| time | L | a | b | ΔE | time | L | a | b | ΔE |
| 0 | 61.08 | 1.86 | 14.35 | 0 | 0 | 61.08 | 1.86 | 14.35 | 0 |
| 2 | 50.07 | 7.12 | 25 | 16.20 | 2 | 55.11 | 3.00 | 13.48 | 6.14 |
| 5 | 47.53 | 9.45 | 20.04 | 21.38 | 5 | 54.48 | 3.19 | 12.30 | 7.04 |
| 10 | 45.45 | 10.63 | 30.59 | 24.19 | 10 | 53.06 | 3.60 | 11.17 | 8.80 |

The above results illustrate that when the dye composition of the invention in a Level 8 brown shade is combined with the hydrogen peroxide composition as described above, the ΔE at 2, 5, and 10 minutes for the compositions of the invention is significantly greater than the ΔE for L'Oreal Feria haircolor at the same time intervals. Thus, the claimed dye composition is capable of depositing more color on the hair in a shorter period of time than the L'Oreal Feria product.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. An aqueous hair color composition for oxidatively coloring hair in twelve minutes or less, wherein said composition is prepared by combining a dye mixture and a developer mixture, said aqueous hair color composition comprising:
    a) 0.01–2.0% (combined weight) of the total composition of primary intermediates and couplers,
    b) a free alkalinity concentration of 0.20–0.75 meq/gram; and
    c) a hydrogen peroxide concentration of 4.0–6.0% by weight of the total composition.

2. The composition of claim 1 which provides Level 1 through Level 10 haircolor.

3. The composition of claim 2 which provides Level 1 haircolor.

4. The composition of claim 3 wherein the combined weight of the primary intermediates and couplers is 0.9–1.9% by weight of the total composition.

5. The composition of claim 3 wherein the free alkalinity concentration is 0.20 to 0.34 meq/gram.

6. The composition of claim 3 wherein the hydrogen peroxide concentration is 4.6 to 5.5% by weight of the total composition.

7. The composition of claim 2 which provides a Level 2 haircolor.

8. The composition of claim 7 wherein the combined weight of primary intermediates and couplers is 0.8–1.8% by weight of the total composition.

9. The composition of claim 7 wherein the free alkalinity concentration is 0.20 to 0.34 meq/gram.

10. The composition of claim 7 wherein the hydrogen peroxide concentration is 4.6 to 5.5% by weight of the total composition.

11. The composition of claim 2 which provides a Level 3 haircolor.

12. The composition of claim 11 wherein the combined weight of primary intermediates and couplers is 0.7–1.7% by weight of the total composition.

13. The composition of claim 11 wherein the free alkalinity concentration is 0.34 to 0.52 meq/gram.

14. The composition of claim 2 which provides Level 4 haircolor.

15. The composition of claim 14 wherein the combined weight of primary intermediates and couplers is 0.6–1.6% by weight of the total composition.

16. The composition of claim 14 wherein the free alkalinity is 0.34 to 0.52 meq/gram.

17. The composition of claim 2 which provides Level 5 haircolor.

18. The composition of claim 17 wherein the combined weight of primary intermediates and couplers is 0.5–1.5% by weight of the total composition.

19. The composition of claim 17 wherein the free alkalinity is 0.52 to 0.64 meq/gram.

20. The composition of claim 2 which provides Level 6 haircolor.

21. The composition of claim 20 wherein the combined weight of primary intermediates and couplers is 0.4–1.2% by weight of the total composition.

22. The composition of claim 20 wherein the free alkalinity is 0.52 to 0.64 meq/gram.

23. The composition of claim 2 which provides Level 7 haircolor.

24. The composition of claim 23 wherein the combined weight of primary intermediates and couplers is 0.3–1.0% by weight of the total composition.

25. The composition of claim 23 wherein the free alkalinity is 0.52 to 0.64 meq/gram.

26. The composition of claim 2 which provides Level 8 haircolor.

27. The composition of claim 26 wherein the combined weight of primary intermediates and couplers is 0.2–0.8% by weight of the total composition.

28. The composition of claim 26 wherein the free alkalinity is from 0.52 to 0.64 meq/gram.

29. The composition of claim 2 which provides Level 9 haircolor.

30. The composition of claim 29 wherein the combined weight of primary intermediates and couplers is 0.1–0.6% by weight of the total composition.

31. The composition of claim 29 wherein the free alkalinity is 0.52 to 0.64 meq/gram.

32. The composition claim 2 which provides Level 10 haircolor.

33. The composition of claim 32 wherein the combined weight of primary intermediates and couplers is 0.01–0.30% by weight of the total composition.

34. The composition of claim 32 wherein the free alkalinity is 0.64 to 0.75 meq/gram.

* * * * *